United States Patent [19]

Niemelä Seppo

[11] Patent Number: 4,865,987
[45] Date of Patent: Sep. 12, 1989

[54] THERMAL GRADIENT-INCUBATOR
[75] Inventor: Niemelä Seppo, Helsinki, Finland
[73] Assignee: Limitek OY, Finland
[21] Appl. No.: 167,258
[22] Filed: Mar. 11, 1988
[30] Foreign Application Priority Data
  May 15, 1987 [FI] Finland ................................. 872153
[51] Int. Cl.[4] .............................................. C12M 1/38
[52] U.S. Cl. ................................... 435/290; 435/281; 435/316; 165/170
[58] Field of Search ............... 435/284, 286, 316, 290, 435/287; 165/170

[56] References Cited
U.S. PATENT DOCUMENTS
4,195,131 3/1980 Popas .................................. 435/316
4,584,275 4/1986 Okano et al. ......................... 435/290
4,666,853 5/1987 Meseral et al. ...................... 435/287

Primary Examiner—Larry Jones
Attorney, Agent, or Firm—Woodard, Emhardt, Naughton, Moriarty & McNett

[57] ABSTRACT

The invention relates to a thermal gradient-incubator for studying and monitoring the temperature-dependent growth and other activity of microbes, comprising a rectangular, highly heat-conductive gradient plate (1) whose longer side edges are fitted with temperature conditioning means (2), extending substantially along the entire length of the longer side edges of gradient plate (1). The temperature conditioning means (2) are heated or cooled by means of fluid circulation, electricity or the like operating on a counterflow principle.

10 Claims, 3 Drawing Sheets

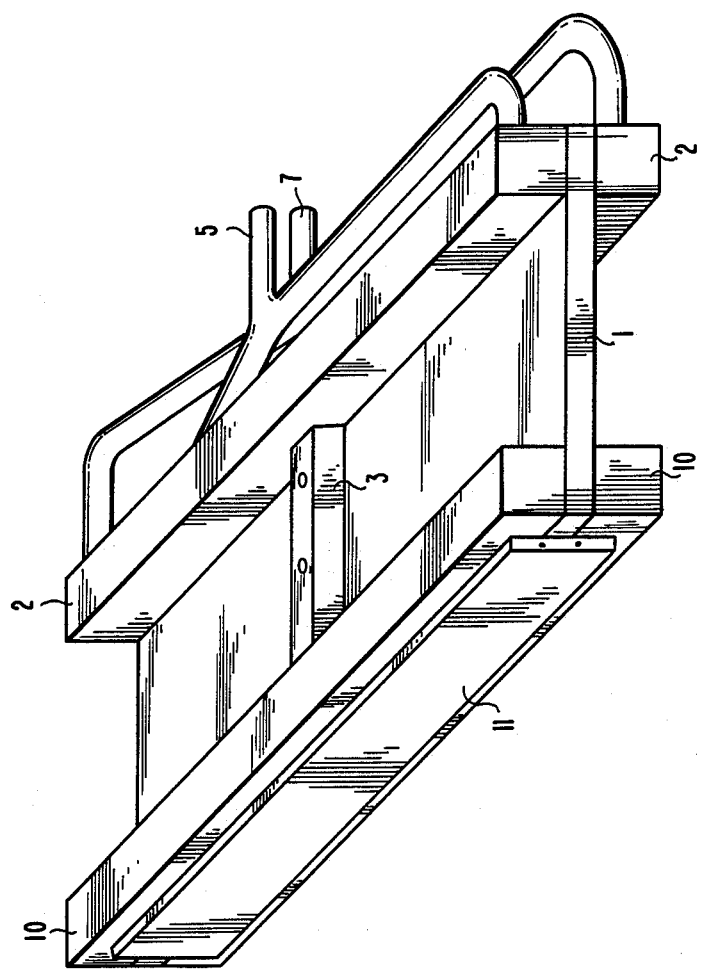

THERMAL GRADIENT-INCUBATOR

The present invention relates to a thermal gradient-incubator intended for studying and monitoring the temperature-dependent growth and other activity of microbes, comprising a gradient plate provided by a rectangular, thermally highly conductive plate, such as a metal sheet, whose two opposite long edges are fitted with temperature conditioning means.

When studying the dependence of biological activities on temperature, thermal gradient-incubators are useful devices in a variety of ways. In nearly all solutions disclosed in literature, a temperature gradient is obtained by heating one end of an elongated metal body to a constant temperature. The other end is either subjected to free cooling or cooled to a constant temperature. By virtue of heat conduction, the metal body generates a more or less linear temperature gradient which can be utilized for studying the growth and activity of microbes at continuously varying temperatures.

There are two main types of thermal gradient-incubators described in literature and intended for microbiological application. Some are intended for growing microbes in fluid cultures, some for growing in agar jelly or other "solid" culture medium. In the latter type, it is possible to effect a stepless or continuous temperature gradient. A typical characteristic for the geometry of the available equipment is that temperature varies along the greatest dimension of a metal body, whereby the temperature distribution in lateral or isothermic direction is automatically sufficiently conditioned. If the culture capacity should be increased in lateral direction, either the temperature distribution becomes difficult to control or the equipment becomes bulky if the longitudinal direction is still to be maintained as the direction of gradient. In general, the capacity of the prior art thermal gradient-incubators is from one culture to a few cultures per run.

An object of the invention is to develop an improved thermal gradient-incubator capable of producing an increased culturing capacity in relation to the size of an apparatus without losing an exact orthogonal temperature field.

According to the invention, these objects are achieved by providing two separate temperature conditioning means to extend in the direction of the longer dimension of a gradient plate and in a manner that at least the fluid flows, led into the second conditioning means in heat conductor elements aligned with each other on the opposite sides of a gradient plate, are oppositely directed to each other, which has been resolved by forking the conditioning fluid inlet pipe into two pipe branches, which are connected to the opposite ends of heat conductor elements aligned with each other on the opposite sides of a gradient plate and the ends of the outlet pipe branches are connected to the opposite ends of the same heat conductor elements also on the opposite sides of a gradient plate.

The increase of capacity is achieved by 1) extending a gradient plate relative to the gradient in lateral direction and by 2) double-sided utilization of a gradient plate. This leads to difficulties in maintaining the isotherms straight and perpendicular to the gradient and these problems have been resolved by applying a counterflow principle in the temperature conditioning means.

Thus, the two separate temperature conditioning means are adapted to extend in the direction of the longer dimension of a gradient plate and mounted in the direction of the shorter dimension of a gradient plate at such a distance from each other, which is substantially shorter than the length of the temperature conditioning means and/or the longer dimension of a gradient plate. As these two separate temperature conditioning means are arranged according to the above geometry and provided with a uniform temperature on a counterflow principle or electrically together with a counterflow principle, the thermal gradient can be distributed precisely and in a controlled manner over the entire area of a gradient plate, which is therefore effectively exploited.

A few embodiments of the invention will now be described in more detail with reference made to the accompanying drawings, in which FIG. 1 shows a gradient-incubator of the invention or rather an incubator core section of the invention in perspective view.

FIG. 3 is fitted in a thermally insulated housing.

FIG. 3 is a perspective view of an incubator core section according to another embodiment of the invention.

One section of an incubator apparatus is provided by a highly heat-conductive gradient plate 1, preferably a rectangular metal plate. The opposite long edges of plate 1 are provided with unequal constant temperatures electrically or by means of fluid circulation. In fluid circulation, fluids are pumped through hollow heat conductor elements 2 secured on either side to the plate edges, the temperatures of said fluids being conditioned externally of the apparatus in thermostated baths. The fluid pipeworks are so designed that an inlet fluid pipe 5 forks into two pipe branches, connected to the opposite ends of heat conductor elements 2 aligned with each other on the opposite sides of a gradient plate. Correspondingly, the ends of the branches of an outlet pipe 7 are connected to the opposite ends of the same heat conductor elements, also on the opposite sides of a gradient plate. Thus, the fluid flows circulate in opposite directions in the internal ducts of heat conductor elements 2 fitted on the opposite sides of a gradient plate. The oppositely directed flows are used to make sure that the temperature of this particular edge of gradient plate 1 is substantially constant over the entire length thereof. Pipes 5 and 7 are connected by hoses to a thermostated bath for conditioning the temperature of a circulated fluid.

Figure 1:
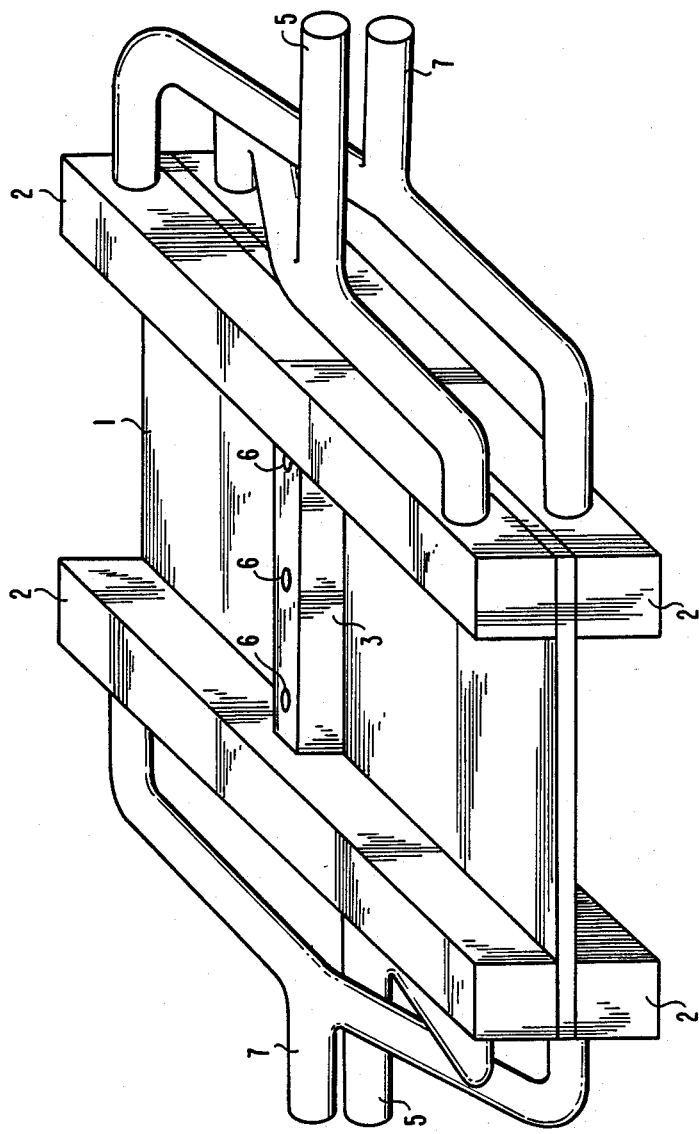

In the case of FIG. 1, the conditioning of temperature at both edges of gradient plate 1 is effected by means of fluid circulation. By selecting the temperatures and temperature differences of fluids it is possible to cover virtually any desired temperature gradient range in the direction of the shorter dimension of plate 1. On the other hand, in the direction of the longer dimension of plate 1, the temperature is substantially constant all the way. In the direction of the shorter dimension of plate 1, the gradient is linear with the exception of extremely narrow marginal zones at the plate edges, which would not be utilized anyway.

FIG. 3 illustrates a case, wherein heat conductor elements 10 at the other edge of plate 1 are heated by means of an electric resistance 11 and the cooling side conditioning means 2 are supplied with fluid flows on a counterflow principle. The cooling side can also be provided with an electric cooling element but the dissipation of heat must be effected by means of conditioning elements, into which the fluid flows are supplied on a counterflow principle.

Figure 2:
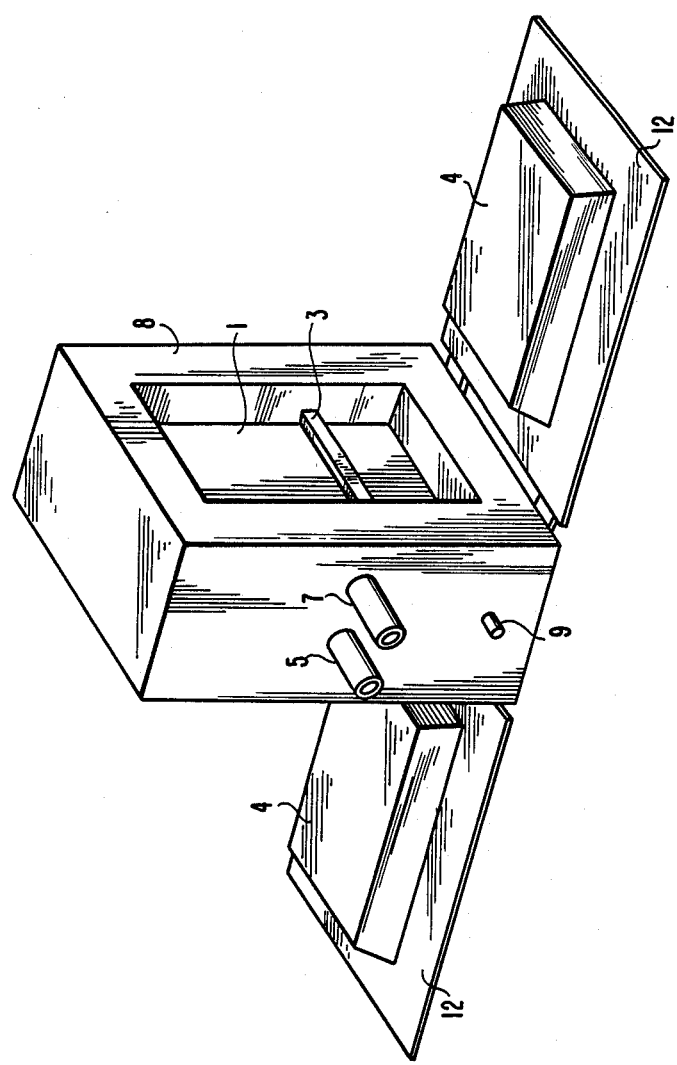
FIG. 2 is a perspective view of an incubator, wherein a core section of FIG. 1

In all embodiments, the thermal gradient is monitored by means of a sensor element 3, comprising two or more electrical measuring sensors 6 mounted at a known distance from each other in the direction of the shorter dimension of a gradient plate. The sensing signals of measuring sensors 6 are used to determine the surface temperatures of gradient plate 1 at precisely known distances from the edges of the apparatus operating area. The linearity of a produced gradient is guaranteed by enclosing the core section of an incubator (FIG. 1 or FIG. 3) in a thermally insulated housing 8 (FIG. 2). Housing 8 opens on two sides, so both sides of gradient plate 1 can be exploited. An operating space heat insulation 4 is fastened to a cover 12.

Pipes 5 and 7 as well as a signal cable lead-in 9 of measuring sensors 6 are passed through the heat insulations of housing 8.

The most important benefits gained by a thermal gradient-incubator of the invention are its compact size, a continuous temperature gradient, an orthogonal temperature field and a high culture capacity. A high capacity is based on the fact that the width of a gradient plate substantially exceeds its gradient-directed length and it can be used in a double-sided manner. On the other hand, the quality of a temperature field is a result of technical solutions in the conditioning means.

What is claimed is:

1. A thermal gradient incubator for studying and monitoring the temperature dependent growth and other activity of microbes comprising:
   a heat conductive gradient plate with a first surface and a second opposite surface, a first end portion, a second end portion opposite said first end portion, a first edge of a first length extending from said first end portion to said second end portion, and a second edge opposite said first edge and having a second length, said plate including a width from said first edge to said second edge less than said first length;
   a first fluid housing mounted to said first edge adjacent said first surface and including a first inlet located at said second end portion and a first fluid outlet located at said first end portion;
   a second fluid housing mounted to said first edge adjacent said second surface and including a second fluid inlet located at said first end portion and a second fluid outlet located at said second end portion;
   an inlet conduit connected to said first fluid inlet and said second fluid inlet allowing flow of a fluid at a first temperature into said first fluid housing and said second fluid housing at opposite ends thereof; and,
   an outlet conduit connected to said first fluid outlet and said second fluid outlet allowing fluid flow from said first fluid housing and said second fluid housing at opposite ends thereof maintaining a constant temperature along said first edge.

2. The incubator of claim 1 and further comprising:
   a third fluid housing mounted to said second edge adjacent said first surface and including a third fluid inlet located at said second end portion and a third fluid outlet located at said first end portion;
   a fourth fluid housing mounted to said second edge adjacent said second surface and including a fourth fluid inlet located at said first end portion and a fourth fluid outlet located at said second end portion;
   a second inlet conduit connected to said third fluid inlet and said fourth fluid inlet allowing flow of fluid at a second temperature different from said first temperature into said third fluid housing and said fourth fluid housing at opposite ends thereof; and,
   a second outlet conduit connected to said third fluid outlet and said fourth fluid outlet allowing fluid flow from said third fluid housing and said fourth fluid housing at opposite ends thereof maintaining a constant temperature along said second edge.

3. The incubator of claim 2 wherein:
   said plate is sized with said first length equaling said second length but greater than said width.

4. The incubator of claim 3 and further comprising:
   temperature sensors mounted to said plate and arranged in a direction extending between said first fluid housing and said third fluid housing being in contact with said first surface.

5. The incubator of claim 4 and further comprising:
   a thermally insulated housing extending circumferentially around said plate and extending outwardly from said first surface and said second opposite surface; and,
   a pair of covers mounted to said housing and extending removably over said first surface and said second opposite surface.

6. The incubator of claim 1 and further comprising:
   electrical heat means mounted to said second edge and operable to control the temperature of said second edge at a constant value different from said first temperature.

7. A thermal gradient incubator comprising:
   a heat conductive gradient plate with a first surface and a second opposite surface, a first end portion, a second end portion opposite said first end portion, a first side of a first length extending from said first end portion to said second end portion, and a second side opposite said first side and having a second length, said plate including a width from said first side to said second side;
   a first fluid housing mounted to said first side adjacent said first surface and including a first fluid inlet located at said second end portion and a first fluid outlet located at said first end portion;
   a second fluid housing mounted to said first side adjacent said second surface and including a second fluid inlet located at said first end portion and a second fluid outlet located at said second end portion;
   an inlet conduit having a pair of interconnected conduits connected respectively to said first fluid inlet and said second fluid inlet allowing flow of a fluid at a first temperature into said first fluid housing and said second fluid housing at opposite ends thereof; and,
   an outlet conduit having a pair of interconnected conduits connected respectively to said first fluid outlet and said second fluid outlet allowing fluid flow from said first fluid housing and said second second fluid housing at opposite ends thereof maintaining a constant temperature along said first side.

8. The incubator of claim 7 and further comprising:

a third housing mounted to said second side adjacent said first surface and including a third fluid inlet located at said second end portion and a third fluid outlet located at said first end portion;

a fourth fluid housing mounted to said second side adjacent said second surface and including a fourth fluid inlet located at said first end portion and a fourth fluid outlet located at said second end portion;

a second inlet conduit having a pair of interconnected conduits connected respectively to said third fluid inlet and said fourth fluid inlet allowing flow of fluid at a second temperature different from said first temperature into said third fluid housing and said fourth fluid housing at opposite ends thereof; and, a second outlet conduit having a pair of interconnected conduits connected respectively to said third fluid outlet and said fourth fluid outlet allowing fluid flow from said third fluid housing and said fourth fluid housing at opposite ends thereof maintaining a constant temperature along said second side.

9. The incubator of claim 8 further comprising:
a thermally insulated housing extending circumferentially around said plate and
a pair of covers mounted to said housing and extending removably over said first surface and said second opposite surface.

10. The incubator of claim 7 and further comprising:
electrical heat means mounted to said second side and operable to control the temperature of said second side at a constant value.

* * * * *